(12) United States Patent
Atanasoska et al.

(10) Patent No.: US 8,182,859 B2
(45) Date of Patent: May 22, 2012

(54) USING MAGNETISM TO PREPARE A MEDICAL DEVICE

(75) Inventors: Liliana Atanasoska, Edina, MN (US); Aiden Flanagan, Galway (IE); Timothy O'Connor, Galway (IE); David McMorrow, Galway City (IE); Robert Nolan, Galway (IE); Anthony Malone, Galway (IE); Jan Weber, Limburg (NL)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1091 days.

(21) Appl. No.: 12/057,135

(22) Filed: Mar. 27, 2008

(65) Prior Publication Data

US 2008/0241351 A1 Oct. 2, 2008

Related U.S. Application Data

(60) Provisional application No. 60/909,200, filed on Mar. 30, 2007.

(51) Int. Cl.
*A61L 33/00* (2006.01)
(52) U.S. Cl. ....... 427/2.24; 427/2.25; 427/2.1; 242/422; 607/1; 623/1.15
(58) Field of Classification Search ................... 427/2.24
See application file for complete search history.

(56) References Cited

U.S. PATENT DOCUMENTS

| | | |
|---|---|---|
| 6,673,104 B2 | 1/2004 | Barry |
| 2004/0030379 A1 | 2/2004 | Hamm et al. |
| 2005/0271696 A1 * | 12/2005 | Dinh et al. ............ 424/423 |
| 2006/0281833 A1 * | 12/2006 | Smith et al. ............ 523/200 |
| 2006/0286137 A1 * | 12/2006 | Sandhu et al. ............ 424/422 |

FOREIGN PATENT DOCUMENTS

| | | |
|---|---|---|
| WO | 2004/093643 | 11/2004 |
| WO | WO 2004/093643 * | 11/2004 |
| WO | 2006/023261 | 3/2006 |

OTHER PUBLICATIONS

International Search Report and Written Opinion, PCT/US2008/058848, Jul. 21, 2008.
Medical Application of Functionalized Magnetic Nanoparticles, Akira Ito et al., Journal of Bioscience and Bioengineering, vol. 100, No. 1, 1-11. 2005.
Pharmaceutical Nanotechnology, Development and characterization of sub-micron poly (D,L-lactide-co-glycolide) particles loaded with magnetite/maghemite nanoparticles, L. Ngaboni Okassa et al., International Journal of Pharmaceuticals 302 (2005) 187-196.

(Continued)

*Primary Examiner* — Doris Lee
(74) *Attorney, Agent, or Firm* — Kenyon & Kenyon LLP

(57) ABSTRACT

The present invention is directed to methods, processes, and systems for delivering therapeutic agent to a medical device. Under some methods, processes, and systems of the invention, particles including a magnetic material and a therapeutic agent may be directed towards a medical device via magnetic attraction. In another embodiment particles including a magnetic material may force a therapeutic agent/solvent solution into porous matrix by using a magnetic attraction. In still another embodiment, a medical device having at least a portion thereof including a magnetic material is used to attract and adhere particles comprising magnetic material and therapeutic agent to a target surface of the medical device, wherein the particles are fused to the target surface.

17 Claims, 14 Drawing Sheets

OTHER PUBLICATIONS

Novel polyelectrolyte multilayer micro- and nanocapsules as magnetic carriers, Andreas Voigt et al., Journal of Magnetism and Magnetic Materials 225 (2001) 59-66.

Radiation effects on poly(lactide-co-glycolide) (PLGA) and poly(L-lactide) (PLLA), Say Chye Joachim Loo et al., Polymer Degradation and Stability 83 (2004) 259-265.

Micron-scale hollow polyelectrolyte capsules with nanosized magnetic $Fe_3O_4$ inside, Dmitry G. Shchukin et al., Materials Letters 57 (2003) 1743-1747.

Responsive polymer films and capsules via layer-by-layer assembly, Svetlana A. Sukhishvili, Current Opinion in Colloid & Interface Science 10 (2005) 37-44.

* cited by examiner

USING MAGNETISM TO PREPARE A MEDICAL DEVICE

CROSS-REFERENCE TO RELATED APPLICATIONS

This application claims priority to U.S. Provisional Application No. 60/909,200, filed Mar. 30, 2007, the disclosure of which is hereby incorporated by reference.

TECHNICAL FIELD

The invention generally regards preparing medical devices that elute therapeutic agent. More specifically the present invention generally regards using magnetism and magnetic attraction to interface or otherwise treat a medical device with therapeutic.

BACKGROUND

The positioning and deployment of medical devices within a target site of a patient is a common, often-repeated procedure of contemporary medicine. These devices, which may be implantable stents and other devices that may be deployed for short or sustained periods of time, may be used for many medical purposes. These can include the reinforcement of recently re-enlarged lumens, the replacement of ruptured vessels, and the treatment of disease, such as vascular disease by local pharmacotherapy, i.e., delivering therapeutic drug doses to target tissues while minimizing systemic side effects. The targeted delivery areas may include body lumens such as the coronary vasculature, esophagus, trachea, colon, biliary tract, urinary tract, prostate, brain, and the like.

Coatings may be applied to the surfaces of these medical devices to increase their effectiveness. These coatings may provide a number of benefits including reducing the trauma suffered during the insertion procedure, facilitating the acceptance of the medical device into the target site, and improving the post-procedure effectiveness of the device.

Coated medical devices may also provide for the localized delivery of therapeutic agents to target locations within the body. Such localized drug delivery avoids the problems of systemic drug administration, such as producing unwanted effects on parts of the body which are not to be treated, or not being able to deliver a high enough concentration of therapeutic agent to the afflicted part of the body. Localized drug delivery may be achieved, for example, by coating portions of the medical devices that directly contact the inner vessel wall. This drug delivery may be intended for short and sustained periods of time.

BRIEF DESCRIPTION

Aspects of the present invention are directed to methods, processes, and systems for interfacing therapeutic agent with a medical device.

In accord with aspects of the invention, a therapeutic agent may be loaded into pores of a porous region of a medical device by providing particles comprising a magnetic material and a therapeutic agent and by using a magnetic field to urge the particles into the pores of the medical device. The particles may be suspended in a solution while the magnetic field is being applied. If the particles are so suspended the imposed magnetic field may diffuse both the solution and the particles into the porous matrix while loading the pores with the therapeutic agent.

The voids and interstices that form the pores and the porous region may be configured to control the elution rate of the therapeutic agent from the medical device. This may include when the medical device is deployed at a target site and when the medical device is being stored, prior to its use.

In accord with aspects of the invention, a target surface of a medical device may also be coated or otherwise interfaced with therapeutic through the use of magnetism to position therapeutic at a target area of the device. The medical device may be coated by positioning the medical device on a holder, activating a magnetic field, and drawing therapeutic to the device through the forces generated by the field. The holder may be configured to mask a non-target surface of the medical device and particles comprising a magnetic core and a therapeutic agent may be employed when coating the device. The therapeutic particles may be attracted by the magnetic force and may adhere to a surface of the medical device. The particles may then be fused to the medical device by applying heat or by some other step.

The invention may be embodied in numerous devices and through numerous methods, processes, and systems. The description provided herein, which, when taken in conjunction with the annexed drawings, discloses examples of the invention. Other embodiments, which incorporate some or all of the features and steps as taught herein, are also possible.

BRIEF DESCRIPTION OF THE DRAWINGS

Referring to the drawings, which form a part of this disclosure:

FIG. 11b shows a particle after removal from the solution of FIG. 11a;

DETAILED DESCRIPTION

Embodiments of the invention may employ magnetism to treat a medical device with a therapeutic. This may include creating micro or nano sized particles of therapeutic around a magnetic particle or core and applying a magnetic field to these particles to interface them with a medical device. This may include driving the particles into pores of the medical device through the use of the magnetic field and gathering quantities of the particles on accessible areas of the medical device and melting the particles together so as to coat the medical device. This may also include placing particles that may be influenced by a magnetic field into a therapeutic and exposing this combination to a magnetic field such that the particles urge the therapeutic towards or into the medical device.

Embodiments of the invention can also include diffusing or otherwise forcing therapeutic agent into one or more voids or spaces of a medical device through the use of magnetism. By loading the medical device in this fashion a greater number of pores of the medical device may be filled than if no magnetic force was used. Magnetic field(s) may be used to force particles, including magnetic material and therapeutic agent, into porous regions of the medical devices. The magnetic field(s) used to force the particles may be alternated or operated simultaneously to drive the therapeutic into the pores. A polymer-free therapeutic may be used in embodiments of the invention to limit inflammation of target tissue of a patient.

Embodiments of the invention can also include coating a target surface of a medical device having a magnetic portion. The medical device may be coated by positioning the medical device on a holder that may be configured to mask a non-target surface of the medical device. For instance, a tubular medical device may be positioned on a balloon catheter which masks the inner diameter of the medical device. Particles having a magnetic material and a shell including a therapeutic agent may be used to coat the device. The particles may be on and around a magnetized surface of the medical device. Once positioned at the target surface of the medical device, the coating particles may be fused to each other and/or the medical device by the application of heat or by other methods.

Figure 1:
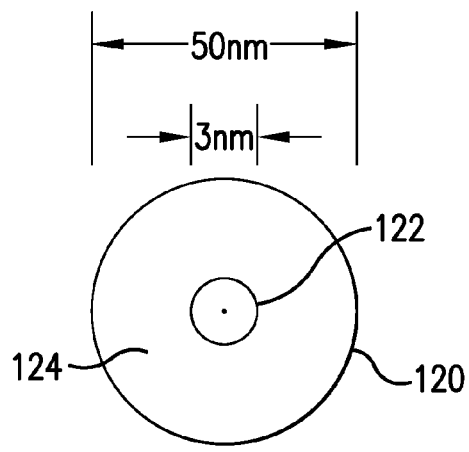
FIG. 1 shows a particle of therapeutic with a magnetic particle.

FIG. 1 shows therapeutic surrounding a particle or core of magnetic material 122. This particle 120 may be spherical as well as other configurations. The particle may contain a therapeutic 124 and may be formed by various processes and some suitable particles are commercially available (e.g., Iron Oxide particles are available through MicroMod™ GMBH).

One process for manufacturing the particles is a ball milling process which may used to reduce magnetite (e.g., $Fe_3O_4$, Iron Oxide, natural magnetic material, etc.) or maghemite (e.g., $Fe_2O_3$) to powder form with individual particles sizes in the micro or nano range. Ball milling may be used for powder reduction whereby a cup loaded with the substrate and some balls of a relatively hard material such as tungsten carbide may be rotated at high speeds. Centrifugal force causes the balls to pulverize the substrate material until it has been reduced to powder form.

In another process, a sputtering magnetron gun may be used to synthesize particles. The gun may employ a high pressure environment of argon gas that facilitates the particle formation due to the atoms colliding. The particles may be captured in the gas flow and can then emerge out through an aperture in an inert atmosphere (e.g., a couple of milli-torrs). Iron nano-particles, for example, in the range of 10-50 nm, may be produced with the gun.

In yet another process the particles may be made from a biopolymer such as dextran or chitosan. The biopolymer may be functionalized having OH—COOH or other groups to which the drug may be connected.

Still another process may be used to create particles, such as a cobalt-nickel alloy, by refluxing an ethylene glycol solution of the particle acetates containing PVP. For example, in order to obtain alloy particles of the composition Co 90%, Ni 10%, a mixture of Co (acetate) and Ni (acetate) may be dissolved in a volume of ethylene glycol and refluxed at approximately 200° C. for about 10 hours. At the end of the reaction, the particles may be precipitated by adding excess water and isolated by centrifugation.

Other processes for making particles in the micro or nano range may also be used.

In the example shown in FIG. 1, the particle may be about 50 nm in diameter and may have a core of 3 nm, however, other dimensions are possible. For example, in some instances, cores of up to 30 nm may be used. The outer shell of the particle may have a higher surface tension that aids in keeping its shape. The outer shell may also comprise a different material, which may be used to encapsulate the therapeutic and core. An abundant amount of these particles may be made and they may be used to coat or otherwise treat medical devices without or without other coating systems including polymeric systems.

Figure 2:
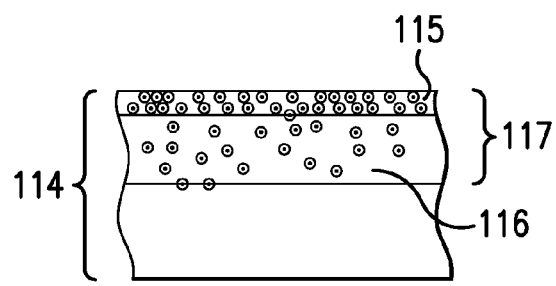
FIG. 2 shows a section of a medical device that has been treated in accord with an embodiment at the present invention.

FIG. 2 shows the invention where particles having magnetic cores are placed on and around a medical device 114 with a porous region. The particles may naturally wick down through an outer area 115 of the device without the aid of additional forces. Should a magnetic force be created around the device, this force may act on the particles to drive the therapeutic further down into the device. The additional depth of treatment is shown in area 117. Noticeable in this figure is that the therapeutic may be become less dense as the therapeutic moves into the device. This density, however, may be different in other embodiments. Also, while therapeutic is shown in discrete particulates, it may also be driven by suspending magnetic particles into a therapeutic and then applying this mixture to the surface of the device and allowing magnetic forces to urge the magnetic particles into the device, bringing the therapeutic along as they migrate into the device.

Figure 3:
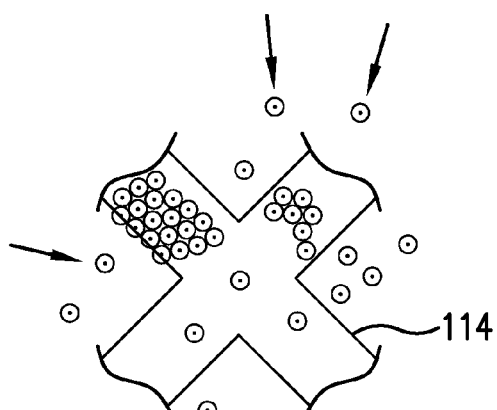
FIG. 3 shows a section of a medical device being treated in accord with embodiments of the present invention.
Figure 4:
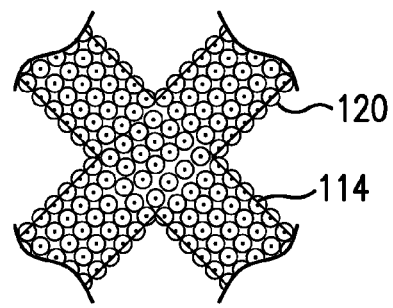
FIG. 4 shows a section of a medical device being treated in accord with embodiments of the present invention.
Figure 5:
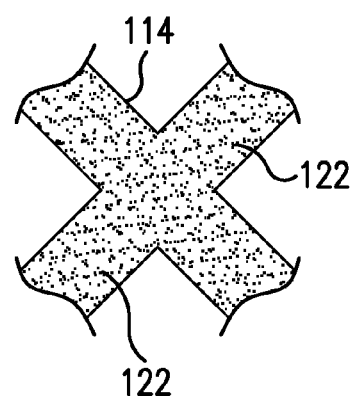
FIG. 5 shows the section of a medical device from FIG. 4 after it has been treated in accord with an embodiment of the present invention.

FIGS. 3-5 show the use of magnetism to draw therapeutic to specific areas of a medical device to be coated. In this example, the medical device 114 has magnetized portions that draw the magnetic cores or particles 122 towards the device. Once lodged on the device, the outer boundaries of the particles 120 may be removed, dissolved, or become otherwise indistinguishable, and a coating of therapeutic and magnetic particles 122 may remain. In some embodiments, this coating methodology may be accomplished without the use of a polymer. In some embodiments, the magnetic particles may be removed as well.

Figure 6:
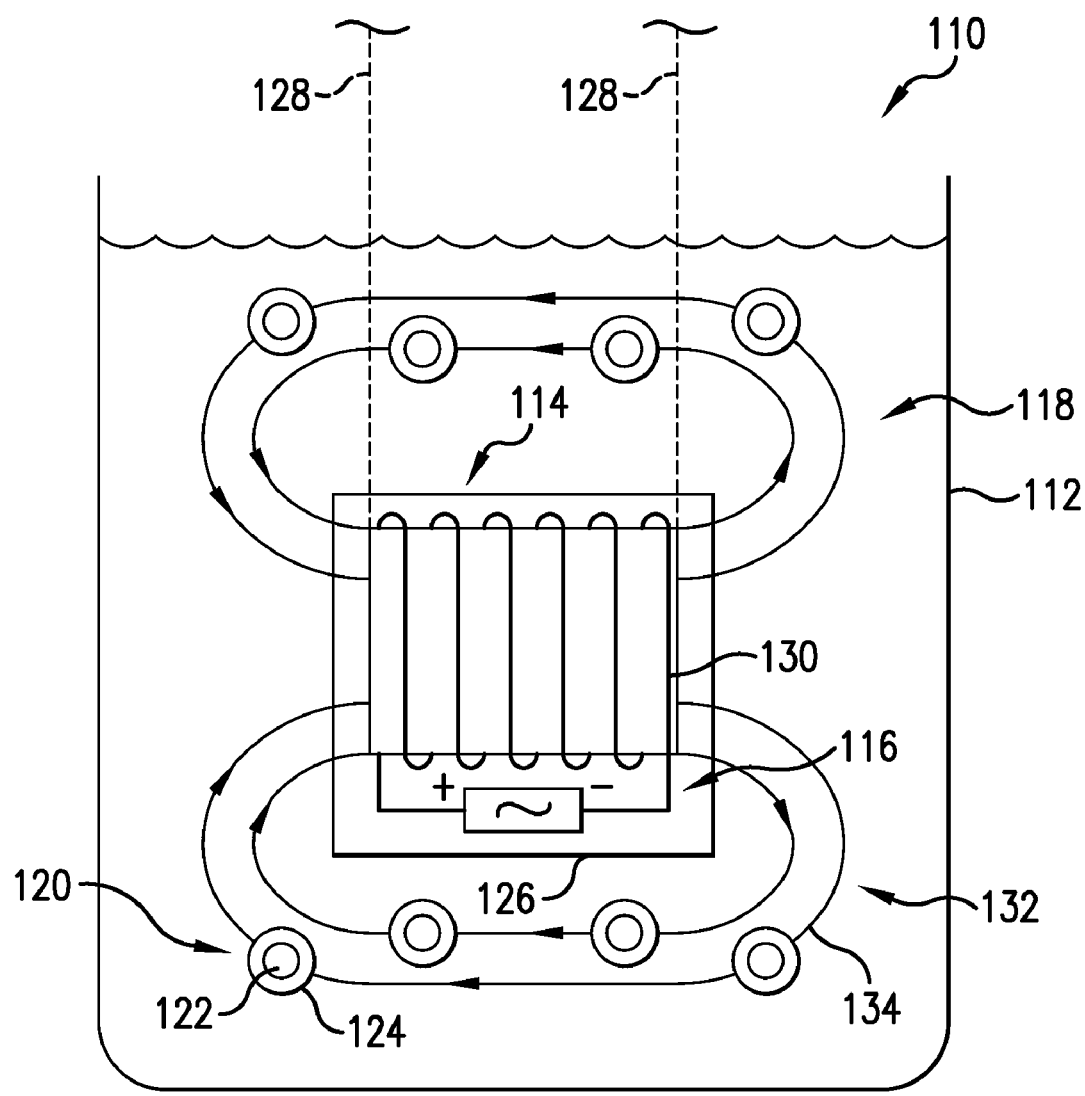
FIG. 6 shows a magnetic field being applied to a medical device in accord with embodiments of the present invention.
Figure 7A:
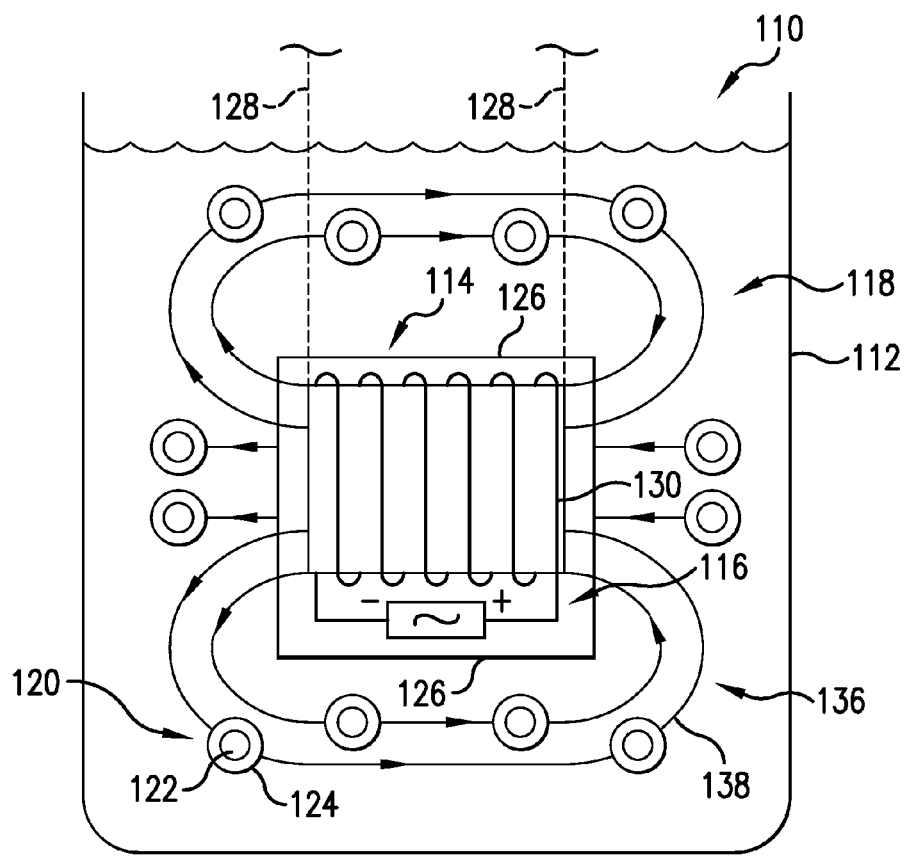
FIG. 7a shows an alternate magnetic field being applied to the medical device of FIG. 6 as may be employed in accord with the present invention.

In FIGS. 6 and 7a, a system 110 for loading therapeutic agent into a porous region of a medical device is depicted. The system generally comprises a cell 112, a medical device 114, and a electromagnet 116. The exemplary embodiments of FIGS. 6 and 7a show the medical device 114 immersed in a solution 118, however, other conventional coating techniques such as spraying (FIG. 5) and dipping may be used. Likewise, the particles may also be interfaced with a powder, instead of a solution, to diffuse both the powder and the particles into the porous matrix while loading the pores with the therapeutic agent. For example, the particles may be interfaced with the powder in a controlled air environment and/or in a vacuum.

As best seen in FIGS. 6 and 7a, the cell 112 contains the solution 118 having suspended particles 120. In the example, the particles 120 have a core comprised of magnetic particle 122 and a shell including a therapeutic agent 124, however, other arrangements are possible. For example, a therapeutic agent core and shell comprised of magnetic material may also be used. Still further, biocompatible (e.g., chitosan) layer(s) may also be used in conduction with the therapeutic agent and magnetic particle. The size of the coating particles may vary. In some instances, the coating particles may be nanoparticles, for example, in the range of 500 nm or less in diameter to enable further depth of impregnation of the porous region. The magnetic particle may be 50 nm or smaller and may be comprised of any suitable materials that exhibit magnetic properties. For example, ferromagnetic materials such as iron, cobalt, nickel, and various combinations of the same may be used. Super-paramagnetic materials may also be used, for example, magnesium ferrite may be used.

The entire medical device 114 shown in FIG. 6 may be porous, however, as discussed herein below, other arrangements are possible. The medical device 114, in this case a stent, may be suspended in the solution 118 by wires 128. Although wires 128 are shown for supporting the medical device 114 within the solution 118, it will be appreciated that a variety of holding devices can be designed to suspend the medical devices 114 while minimizing interference and permitting access to portions of a target surface of the medical device 114. For example, alligator clips and mandrels are suitable devices which may limit contact with target surfaces of medical devices.

FIGS. 6 and 7a show an electromagnet 116. The electromagnet 116 generally comprises an electrical conduit 130 which may be electrically connected to a voltage source 126. Both AC and/or DC sources are suitable.

The particles may be attracted towards the direction of a higher magnetic flux, aligned with their poles, along the magnetic field lines. The movement of the particles may arise from the that fact that one pole is closer to a magnetic field source than the other, thus resulting in a net magnetic force. The medical device may be placed in a solution containing the magnetic particles, that has magnetic field lines running therethrough (with increasing field strength towards the medical device). Consequently, as the particles are attracted towards the magnetic source, the particles meet a surface of the medical device and can be pushed/pulled into the porous matrix. In some instances, a static magnetic field of a few Tesla may be used to overcome frictional forces that may limit and/or prevent particles from penetrating deep into the porous matrix.

This vibration may be mechanical vibration of the stent or may be an additional AC component to the magnetic field created perpendicular to the main magnetic field. In other words, the magnetic field may be separated into a static and a dynamic vector, whereby the dynamic component is not along the same direction as the static component The medical device may be loaded in a variety of ways. For instance, in one example, one side may be loaded, the particles melted together and/or the side sealed to block their exit, and an opposite side loaded. Still other loading arrangements are possible.

As seen in FIG. 6, electrons flow from the negative to positive side of the electromagnet 116. Consequently, a magnetic field 132 having magnetic field lines 134 may be created around the electrical conduit 130 in a direction generally parallel to the electron flow. In FIG. 7a, the electrons also flow from the negative to positive side of the electromagnet 116, however, the poles of electromagnet 116 are reversed, which in turn changes the direction of the magnetic field 136 and magnetic field lines 138.

Figure 15:
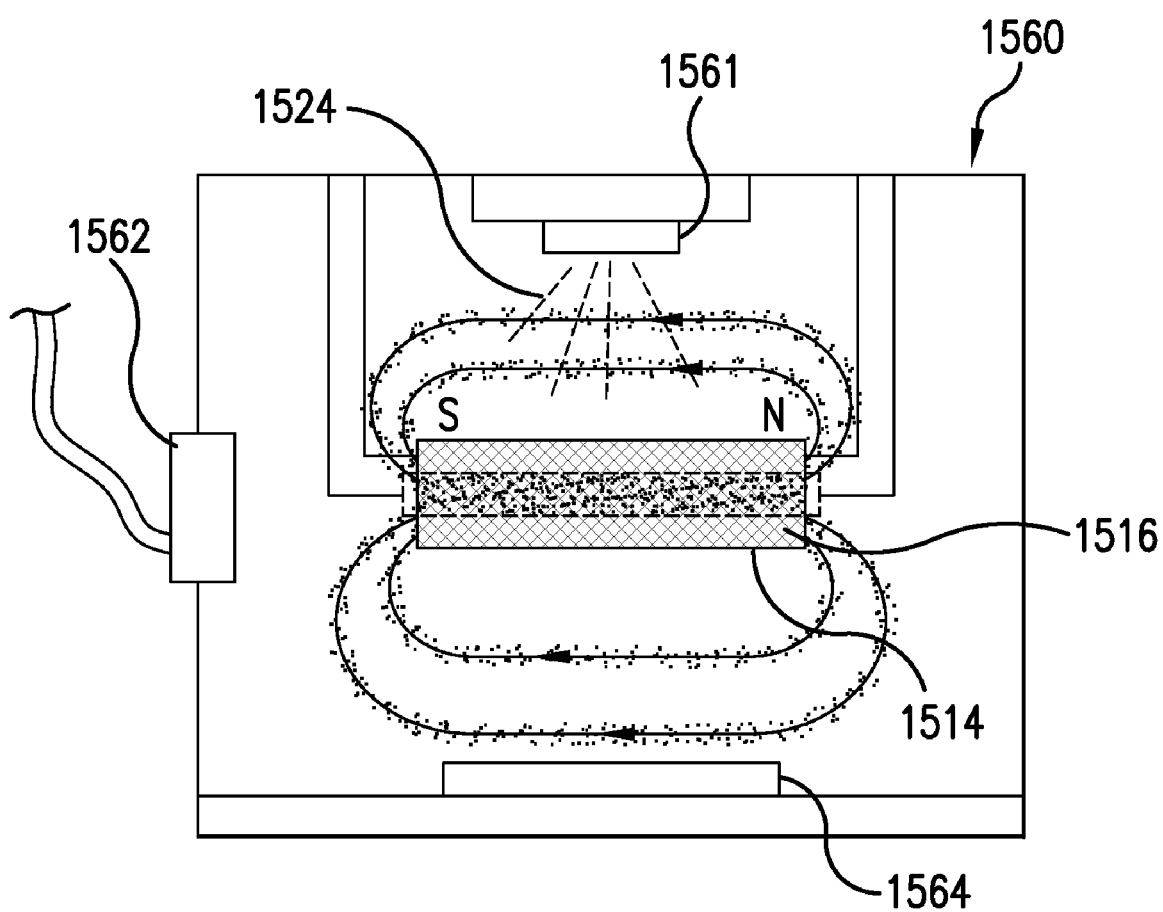
FIG. 15 shows a medical device being loaded with therapeutic inside a treatment chamber as may be employed in accord with the present invention.

While an electromagnet is shown in the examples, any suitable objects that produce a magnetic field may be used. For example, permanent magnets such as bar magnets may be used (FIG. 15).

The electromagnet 116 of FIGS. 6 and 7a acts in the similar manner to a permanent magnet, except, the magnetic fields 132, 136 only exist when electric current is flowing through the electrical conduit 130. In FIGS. 6 and 7a, the voltage source shown is a battery.

Consequently, since the particles 120 of FIGS. 6 and 7a comprise magnetic particles 122, when the voltage source 126 is energized, magnetic fields 132, 136 are created and the particles 120 are attracted to and diffused along the magnetic field lines 134, 138. Although one electromagnet is shown in FIGS. 6-7, other arrangements are possible. For example, a plurality of electromagnets may be used simultaneously or in alternating arrangements. Likewise, the magnetic fields 132, 136 created from electromagnet 116 may be alternated or configured to operate simultaneously to facilitate loading of therapeutic agent within the porous region of the medical device 114.

In use, the system may be used to load a porous region of a medical device 114 with therapeutic agent 124 by applying a magnetic field 132, 136. The electromagnet 116 and at least the target portion of the porous stent are positioned within the cell 112 containing the solution 118 and the particles 120. Current is then applied to the electromagnet 116. As the magnetic field 132, 136 is applied, the particles 120, which comprise the magnetic material, wiggle and/or vibrate as they are attracted to and move along the magnetic field lines 134, 138. As this diffusion of the particles 120 occurs, some, or all of the particles 120 enter the plurality of pores of the porous matrix and may be entrapped. In FIGS. 6 and 7a, the therapeutic agent 124 enters the pores by being attached to the particles 120.

Figure 7B:
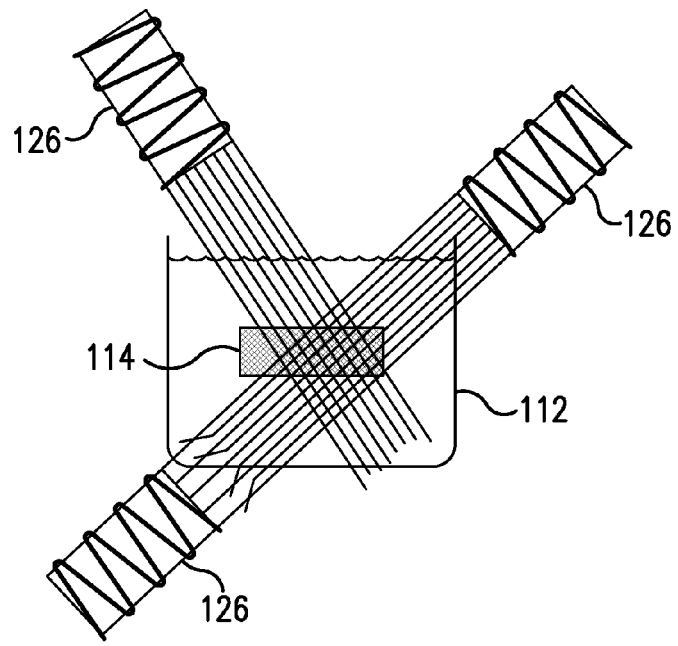
FIG. 7b shows magnetic fields being applied to a medical device as may be employed in accord with the present invention.

Also in accord with an embodiment of the present invention, FIG. 7b shows magnetic fields being applied to a medical device 114. In FIG. 7b, a cell 112 and three electromagnets 116 are shown, however, any number of electromagnets 116 may be used. The electromagnets 116 may be turned on and off, as desired, to enable varying motions of the magnetic particles. Alternatively, in some instances, an AC supply may be used and the phases of an electromagnet(s) 116 tuned to each other to create the desired effect.

In FIGS. 6, 7a, and 7b, instead of or in conjunction with using the magnetic field to attract the magnetic particles and therapeutic agent, a vibrating AC field may be used to drive the particles further into the porous matrix.

After the medical devices 114 of FIGS. 6, 7a, and 7b are deployed in the body, there is an absence of vibration, and the particles 120 remain trapped in the porous matrix. Therefore, although the therapeutic agent 124 is still able to migrate through the pores and into the vessel wall or lumen for delivery to a patient, the rate of migration is reduced at least by the porosity of the porous region. As for the magnetic material, the magnetic material may dissolve within the patient. Therefore, preferably the magnetic material has biocompatible properties.

A multitude of parameters may be varied to achieve a wide range of therapeutic agent elution times. For example, parameters which may be varied include, but are not limited to, immersion time of the medical device in the solution, pore density and connectivity, the frequency/strength of the magnetic fields applied, the viscosities of the solutions, solvents, and therapeutic agents used, and temperatures which may be used throughout the process. For example, in some instances, the temperature may be raised to increase the solubility and the diffusion of the therapeutic agent. In other examples, the frequency of the electromagnetic fields applied may be increased from the radiowave to microwave level to increase diffusion. Yet in still other examples, the frequently may range from DC to several hundred Hz.

The pore density and connectivity may also be varied. The voids and interstices defined in the regions may be various sizes, and may have dimensions in nanometer or micrometer range. These voids and interstices may be homogenous in size and non-homogeneous in size. Also, the porous matrixes may comprise an inert material added to the device as well as the material comprising the device itself.

Figure 8A:
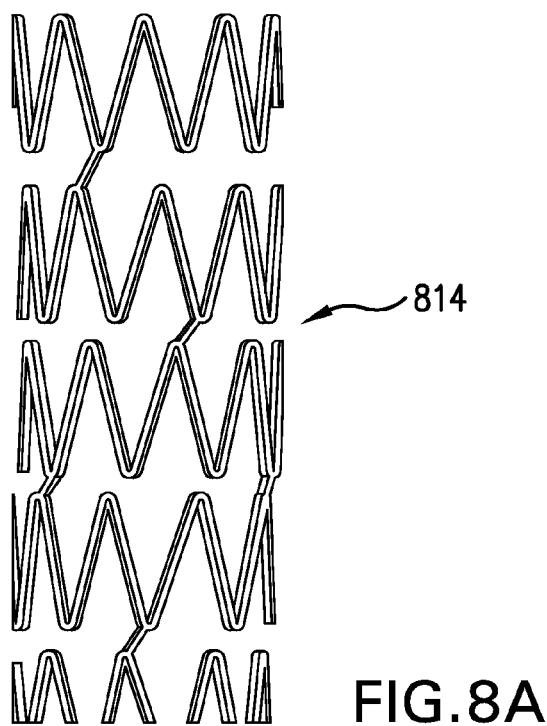
FIG. 8a shows a porous stent comprised of a porous region that may be employed in accord with the present invention.
Figure 8B:
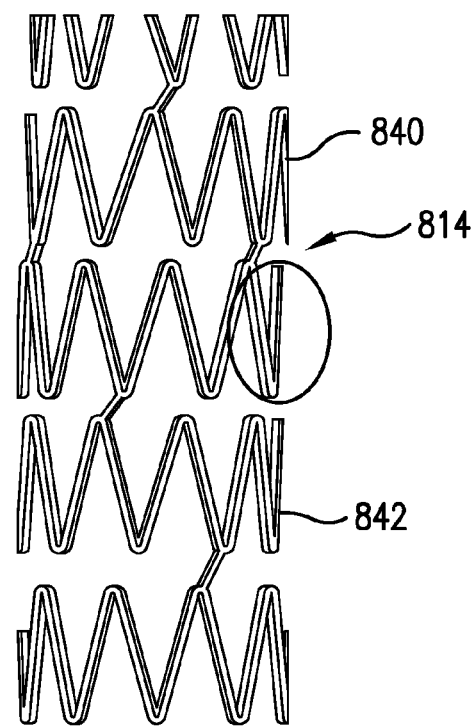
FIG. 8b shows a porous stent having a first porous region and a second porous region that may be employed in accord with the present invention.

As best seen in FIG. 8a, the entire medical device, in this case a stent 814 may be porous and may contain one or more porous regions. For example, as seen in FIG. 8b, a stent with first and second porous regions 840, 842 is provided. FIGS. 8a and 8b illustrate a stent 814 which is composed of a number of struts and links made of a suitable material, such as metal, containing pores. In FIG. 8b, the first porous region 840 may be characterized by a first porosity and first mean pore size configured to receive certain quantities and types of therapeutic agent while the second porous region 842 shown in FIG. 8b may be characterized by a second porosity and a second mean pore size configured to receive different quantities and types of therapeutic agent. Thus, one therapeutic agent may be loaded into the pores of the first porous region 840 and a second therapeutic agent may be loaded into the pores of the second porous region 842. The same therapeutic agent may also be loaded into both the first and the second porous regions 840, 842.

Figure 8C:
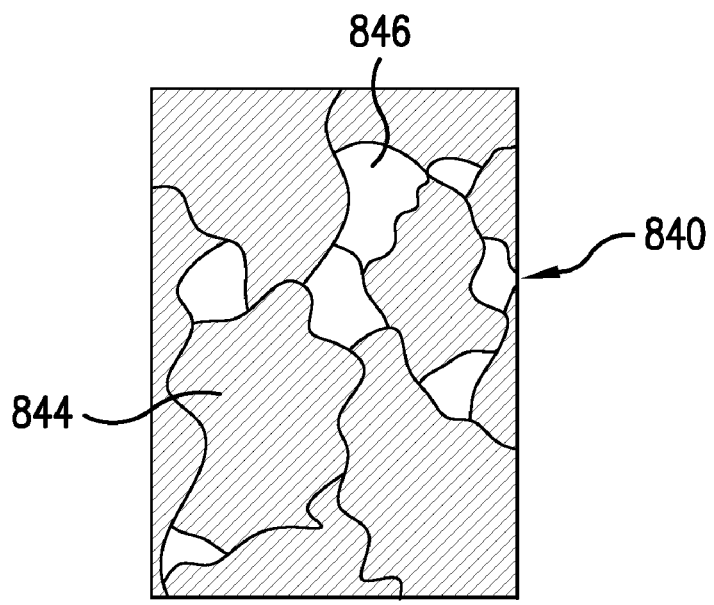
FIG. 8c shows an enlarged view of a portion of the first porous region of the stent of FIG. 8b.

FIG. 8c shows an enlarged view of a portion of the first region 840 of FIG. 8b. As can be seen, the porous region 840 may include particles 844 such as carbon. The particles may include pockets or pores 846 between adjacent particles 844. The proportion of the non-solid volume to the total volume of material may be called the porosity of the particle material. Each pore has a pore size and the rate of drug elution may be controlled by the pore size.

Since the rate of drug elution from a porous region may be determined by the pore size, it may be preferred that the pores are relatively small, for example, as stated herein, in the micrometer or nanometer scale. For example, pore sizes of up to 1 micron may be suitable in certain instances. Smaller size pores may enable sustained therapeutic delivery over a reasonable timescale, for example, about three months. In order to provide enough therapeutic agent to have a therapeutic effect, it may be preferred that all available spaces in the porous layers are loaded with therapeutic agent.

Figure 9:
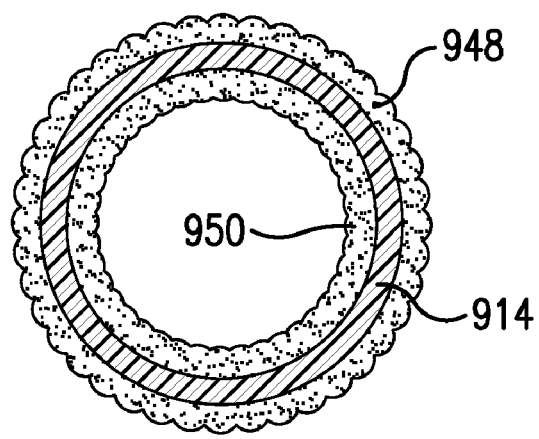
FIG. 9 shows a stent having a first porous layer and a second porous layer as may be employed in accord with the present invention.

Referring to FIG. 9, the medical device 914 may also be formed of a porous layer or layers 948, 950 deposited thereon. The first porous layer 948 may be located on the outside surface of the medical device 914, while the second porous layer 950 may be located on the inside surface of the medical device 914. Also, multiple layers may be placed on top of one another or other surfaces of the stent may have a layer deposited thereon. The porous layer thickness may be any suitable size, for example, coating thicknesses of 1-30 microns are possible.

Porous medical devices may be made from a powdered material such as powdered metal or polymer. The medical devices of the embodiments of the present invention may be formed of any therapeutic-compatible powdered metals such as stainless steel. Other suitable metals include, but are not limited to, spring steel, nitinol and titanium as well as any other therapeutic-compatible metal which may become available in powdered form in the future. Suitable metals typically should not produce toxic reactions or act as carcinogens.

Medical devices that embody the invention may be used for innumerable medical purposes, including the reinforcement of recently re-enlarged lumens, the replacement of ruptured vessels, and the treatment of disease such as vascular disease by local pharmacotherapy, i.e., delivering therapeutic drug doses to target tissues while minimizing systemic side effects. Examples of such medical implants include stents, stent grafts, vascular grafts, and other devices used in connection with therapeutic agent coatings. Such medical devices are implanted or otherwise utilized in body lumina and organs.

The medical implants themselves may be self-expanding, mechanically expandable, or hybrid implants which may have both self-expanding and mechanically expandable characteristics.

FIGS. 10a, 10b, 11a, 11b illustrate various methods that may be employed in accordance with embodiments of the present invention for coating the magnetic material to form the coating particles 1020, 1120.

Figure 10A:
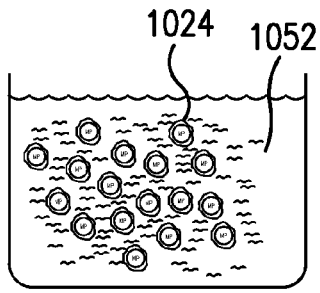
FIG. 10a shows a therapeutic agent being dissolved in a solvent to form a solution as may be employed in accord with the present invention.

As seen in FIG. 10a, prior to coating, the therapeutic agent 1024 (also labeled TA) may be dissolved within a solvent 1052. For example, suitable solvents 1052 include, but, are not limited to dimethylformamide (DMF) and tetrahydroforum (THF). Alternatively, the particles may also be interfaced with a powder, instead of a solution, to diffuse both the powder and the particles into the porous matrix while loading the pores with the therapeutic agent. For example, the particles may be interfaced with the powder in a controlled air environment and/or in a vacuum.

Figure 10B:
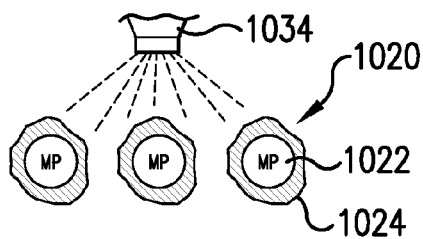
FIG. 10b shows the therapeutic agent/solvent solution of FIG. 10a being used to spray coat a particle as may be employed in accord with the present invention.

Then, as illustrated in FIG. 10b, once the therapeutic agent 1024 has dissolved within the solvent 1052 to form a solution, the solution can be directed at a target surface of the particle 1020 (also labeled MP) comprising magnetic material 1022 for coating with a nozzle 1054. For example, as shown in FIG. 10b, the particles 1020 are being spray coated with the solution, however, other arrangements for coating are possible.

Figure 11A:
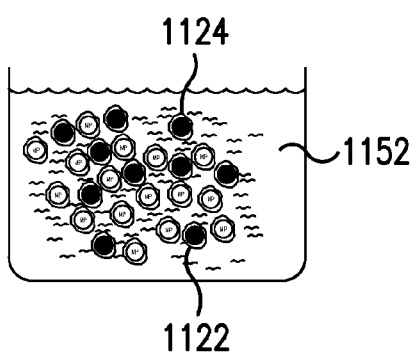
FIG. 11a shows particles being immersed in a therapeutic agent/solvent solution as may be employed in accord with the present invention.
Figure 11B:
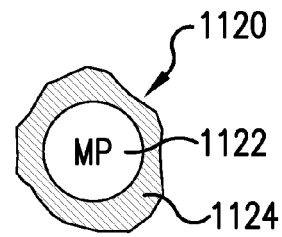

For example, as shown in FIG. 11a, the particles 1120 may be immersed into solution comprised of a solvent 1152 and a therapeutic agent 1124. FIG. 11b shows a particle 1120 that contains a magnetic material 1122 that has been coated with a therapeutic agent 1124 in accordance with the immersion technique of FIG. 11a as may be employed in accordance with embodiments of the present invention.

Figure 12:
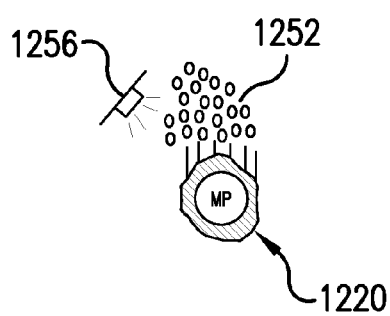
FIG. 12 shows a heating element that may be employed to remove solvent in accord with the present invention.

As may be seen in FIG. 12, a drying step may also be employed if desired to remove excess solvent. The drying step may be employed so that excess solvent 1252 can evaporate from the particle 1220. Any suitable drying time period may be used. In addition, a heating element 1256 may be used to accelerate the solvent evaporation rate from the particle 1220.

Figure 13A:
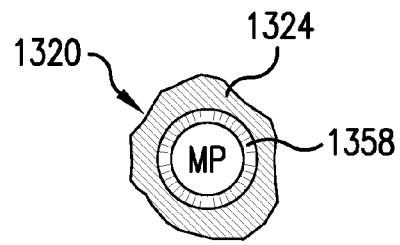
FIGS. 13a-b show therapeutic agent coatings adhered to particles with proteins and amino acids, respectively, as may be employed in accord with the present invention.
Figure 13B:
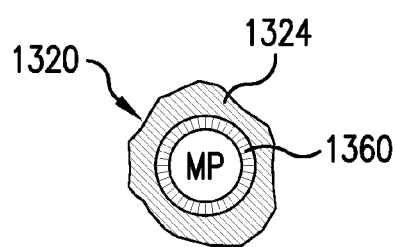

FIGS. 13a and 13b show additional aspects of the invention in which the therapeutic agent may be adhered to a surface of the particle 1320 with a protein 1358 or amino acid 1360 to facilitate controlled release of the therapeutic agent 1324. For example, in FIG. 13a a protein 1358 can be used, and in FIG. 13b an amino acid 1360 may be used. In certain in vitro conditions, the therapeutic agent 1324 may be unable to detach from the particle 1320 until the protein 1358 is cleaved by protein present in the blood. For example, if protein strands are used to adhere the therapeutic agent 1324 to the particle 1320, then in the blood vessel, the protein strands are broken down by plasmin (which is converted from plasminogen by the naturally present tissue plasminogen activator and urokinase). It should be understood that the plasmin can be also be included with the amino strands at the coating stage, or, as noted above, may alternatively be naturally occurring plasminogen in the blood. When the fibrin breaks down, the therapeutic agent 1324 may release from the particle 1320 and elute into the blood vessel.

Figure 14:
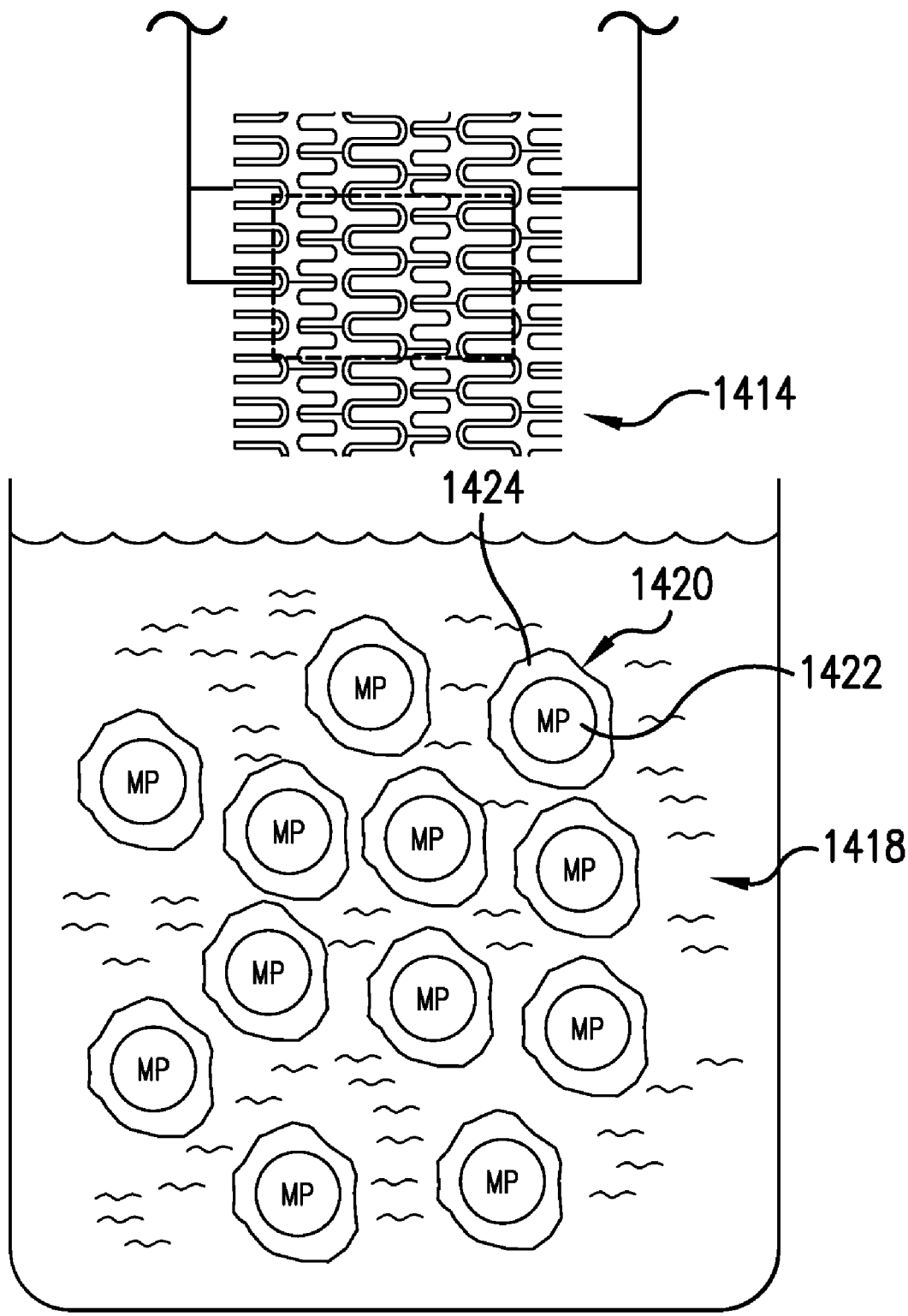
FIG. 14 shows a medical device and a solution having particles suspended therein as may be employed in accord with the present invention.

As illustrated in FIG. 14, following coating, the particles 1420, including the magnetic material 1422, may then be suspended into solvent 1418 (same as solution 118 described in FIGS. 6 and 7a). Any suitable solvent may be used to form the solution, however, preferably the solution does not break down the therapeutic agent 1424. Suitable solvents 1418 include, but are not limited to, water or toluene. The particles 1420 may be loaded within the solution 1418 and target portions of the porous matrix of the medical device 1414 may be loaded therein.

FIG. 15 is similar to FIGS. 6 and 7a, except, a spray nozzle 1561 is being used to load the porous region of the medical device 1514 with therapeutic agent 1524. In addition, a bar magnet 1516 is being used instead of an electromagnet in this example. Permanent magnets have two ends, one marked north and one marked south, for attracting ferromagnetic or ferrimagnetic objects. Therefore, as opposites attract and likes repel, if two bar magnets with their ends marked north and south are lined up proximate to one another, the north end of one magnet will attract the south end of the other. On the other hand, the north end of one magnet will repel the north end of the other. As noted above with reference to FIGS. 6 and 7a, it is within the purview of the embodiments of the invention that permanent magnets, electromagnets, and the like are interchangeable. Likewise, it should be understood for all of the embodiments that any suitable coating technique such as spraying, dipping, and immersing may be used.

Regarding FIG. 15, a treatment chamber 1560 is also shown. The term "treatment chamber" as used herein may be any vessel having defined walls with inside surfaces. A treatment chamber 1560 may be made from various materials including clear, translucent, and opaque polymers, metals, and ceramics. Clear polymers, which provide for the internal viewing of medical devices being coated or impregnated with therapeutic agent in the treatment chamber, may be used in an exemplary embodiment.

In FIG. 15, the treatment chamber 1560 is in fluid communication with a fluid source 1562. In this example, the fluid source is a vacuum source which may facilitate the loading process. The fluid source 1562 may eliminate air trapped within the voids and interstices of the porous matrix to facilitate diffusion of the therapeutic agent 1524. A conventional dryer 1564, such as an infrared heater or convention oven, may also be used to facilitate, for example, evaporation of the solvent from the medical device 1514.

Figure 16:
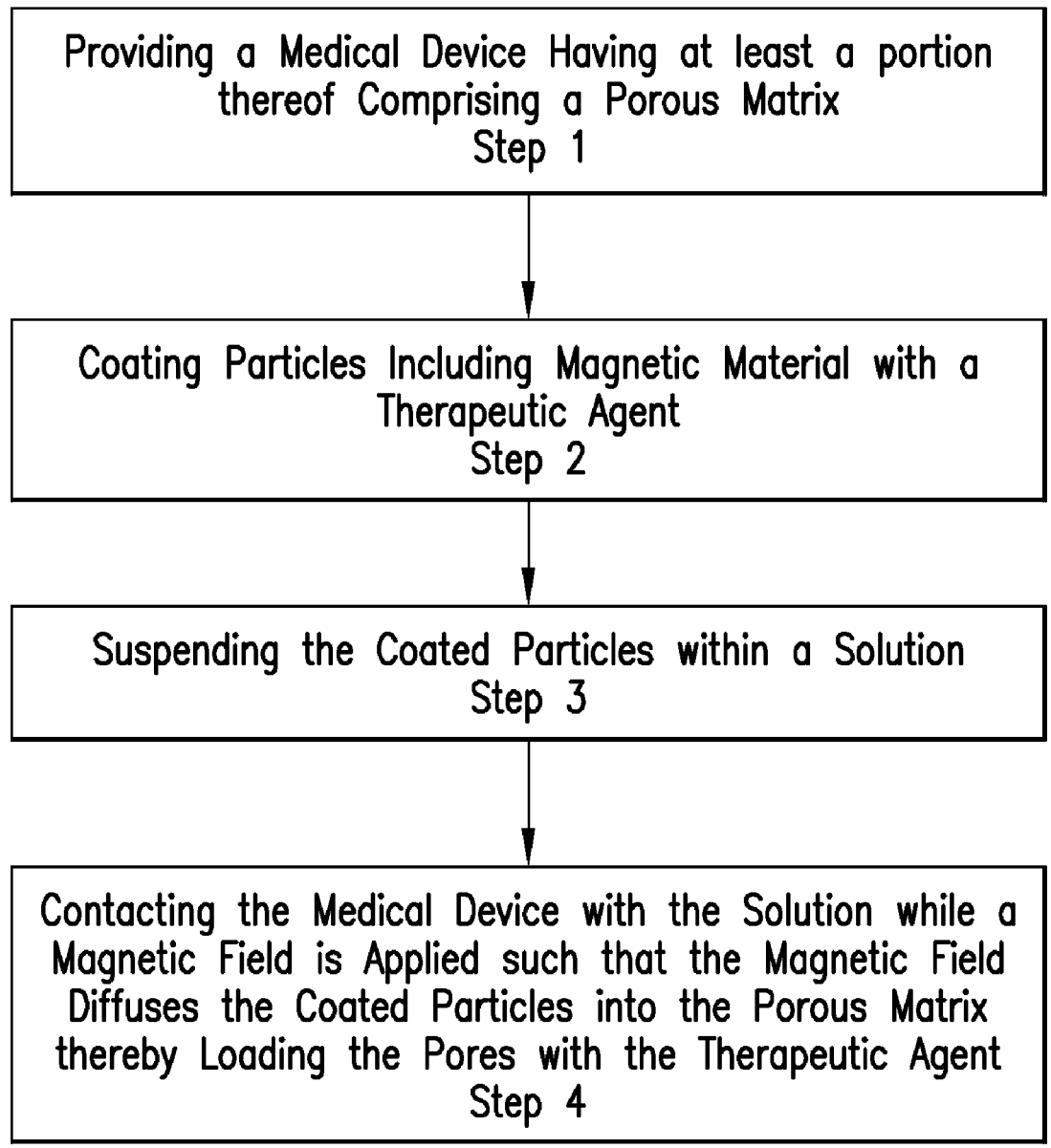
FIG. 16 shows method steps that may be employed in accord with the present invention.

FIG. 16 shows a flow chart including method steps that may be employed with embodiments of the present invention to load therapeutic agent into a porous matrix of a medical device. In the example of FIG. 16, step 1 may include providing a medical device having at least a portion thereof comprising a porous region. Step 2 may include coating particles with a therapeutic agent. Step 3 may include suspending the coated particles into a solution. Step 4 may include contacting the medical device with the solution while a magnetic field is applied such that the magnetic field diffuses the solution into the porous region thereby loading the porous region with the therapeutic agent. In embodiments, not shown, the sequence of steps may be reordered and steps may be added or removed. The steps may also be modified. Further, the steps may be repeated in continuous fashion. For one, particles of magnetic material and therapeutic may be used without a solution, and particles of therapeutic may not be used at all. In this later example, a solution of therapeutic and magnetic particles may be applied to the device.

Figure 17A:
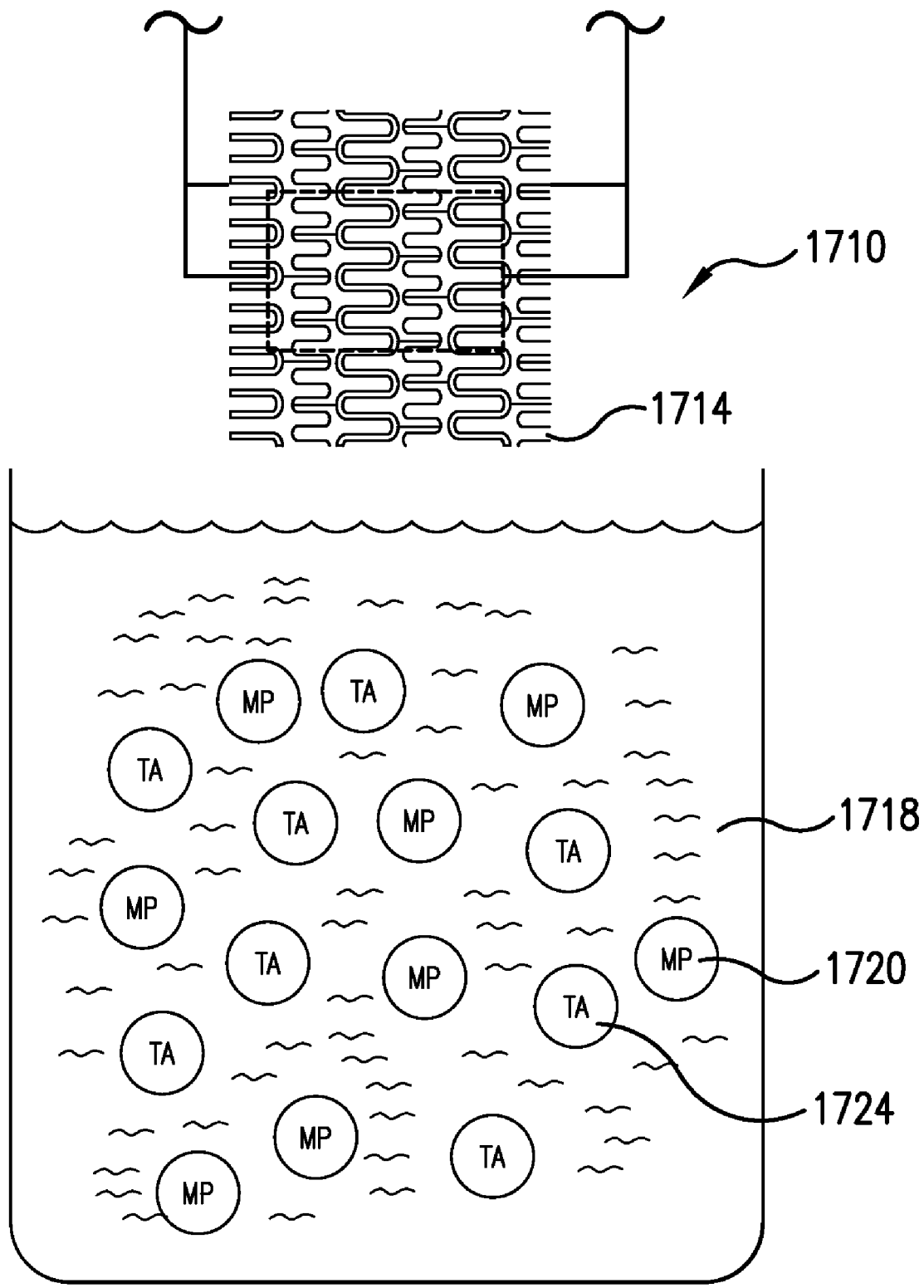
FIG. 17a shows a medical device and a therapeutic agent/solvent solution comprising a therapeutic agent and magnetic material suspended within the therapeutic/agent solution as may be employed in accord with the present invention.
Figure 17B:
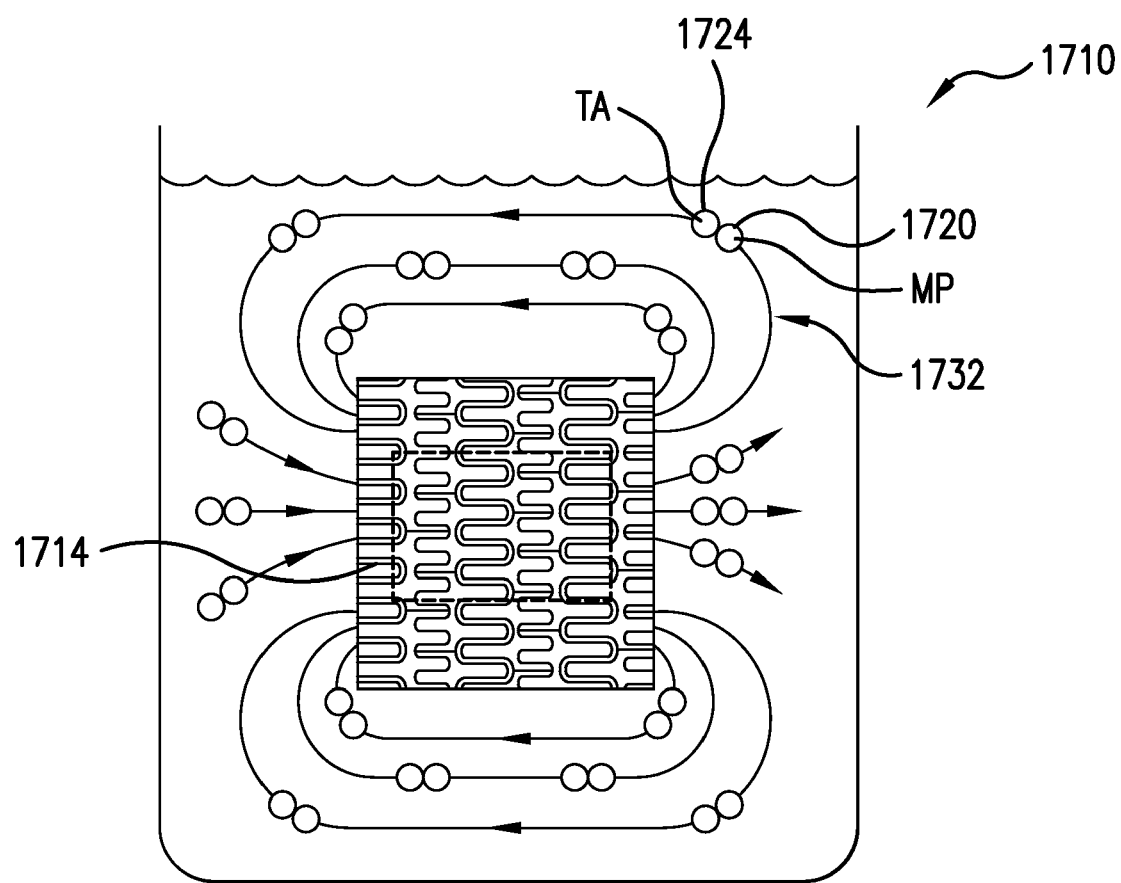
FIG. 17b shows the particles of FIG. 17a forcing the therapeutic agent along magnetic field lines in accord with the present invention.

FIGS. 17a-17b show a system 1710 for loading therapeutic agent 1724 (TA) into a porous region of a medical device 1714 in accord with another aspect of the present invention. In this embodiment, the system 1710 includes a medical device 1714 and a solution 1718 comprising therapeutic agent 1724 and particles 1720 (MP) comprising magnetic material are suspended within the solution 1718. In other words, in this example, the coating particles 1720 are not coated with the therapeutic agent 1724 as in FIGS. 6-7.

Although the therapeutic agent 1724 is dissolved within the solution, the therapeutic agent 1724 is shown in FIGS. 17a-17b for explanatory convenience.

As shown in FIG. 17b, the therapeutic agent 1724 dissolved in the solvent 1718 may surround the particles 1720. Therefore, when a magnetic field 1732 is applied (FIG. 17b), the magnetic material of the particles 1720 may be attracted to the magnetic field 1732 and may vibrate or wiggle in a direction generally parallel to or in close proximity to the magnetic field lines. As a result, the particles 1720 force the solution 1718, in which the therapeutic agent 1724 is dissolved, into the porous region of the medical device 1714. As explained above with reference to FIGS. 6-7, as is the case with this embodiment, the magnetic field(s) may also be alternated or applied simultaneously to improve diffusion of the particles 1720 and the solution 1718 containing the therapeutic agent 1724.

In accordance with still another aspect of the present invention, as may be seen in FIGS. 18-23, another system for coating a medical device is shown. The methods, processes, and systems of this embodiment relate to any medical device 1814 which comprises in at least a portion of its construction a predetermined quantity of a magnetic material or which has been rendered magnetic in another suitable manner, such as coating the medical device 1814 with magnetic material. As will be described in more detail below, in the embodiments of FIGS. 18-23, the medical device 1814 may also be coated with particles 2020 (FIG. 20) comprising therapeutic agent 2024.

Figure 18:
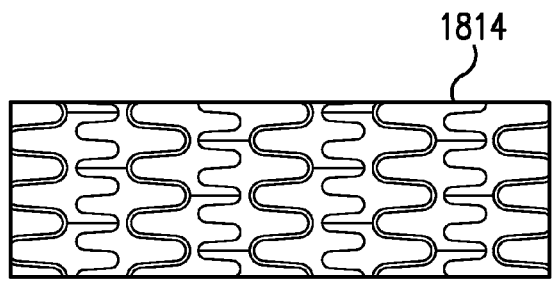
FIG. 18 shows a magnetic stent that may be coated in accord with the present invention.
Figure 19A:
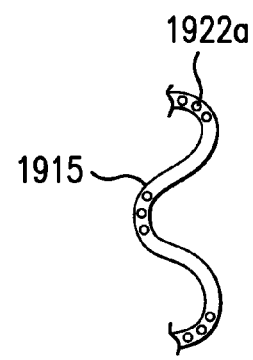
FIG. 19a show a top view of stent having pores configured to receive magnetic material as may be employed in accord with the present invention.
Figure 19B:
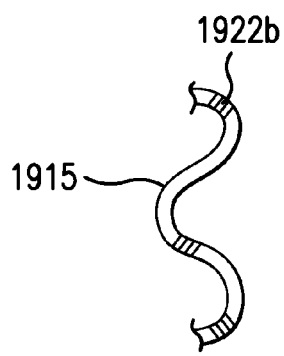
FIG. 19b show a top view of a magnetic stent with portions thereof having a magnetic material layer as may be employed in accord with the present invention.
Figure 19C:
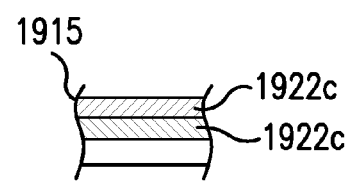
FIG. 19c show a top view of a magnetic stent having magnetic material layers as may be employed in accord with the present invention.
Figure 19D:
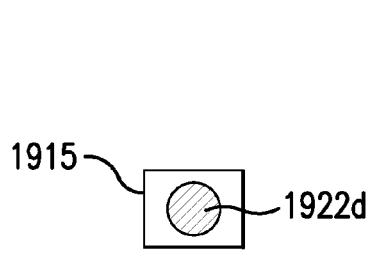
FIG. 19d shows a stent strut having a portion thereof comprising magnetic material as may be employed in accord with the present invention.

As shown in FIGS. 18, 19a-19d, a medical device 1814, 1914, in this case a stent, may be an existing stent which is modified to include magnetic properties or may be a newly constructed stent with magnetic properties. The stent may be made of any conventional stent material including, but not limited to, polymeric materials, metals, ceramics and composites. The entire stent, as shown in FIG. 18, or selective portions thereof, as shown in FIG. 19d, may be manufactured from one or more magnetic materials. For example, a predetermined quantity of magnetite or an alloy thereof may be included in the construction of the medical device. Other materials may be utilized to provide the desired magnetic properties. Such materials may be temporary magnetic materials or permanent magnetic materials.

The medical device may be configured to include magnetic material within a portion of the lattice portion. As best seen in FIG. 19a, the lattice portion 1915 may include one or more chambers or pores which have at least some portion of magnetic material 1922a contained therein. The magnetic material 1922a may be in solid or liquid form. The pores may be filled with magnetic material 1922a, and then optionally coated with a biocompatible coating. Another means of providing a medical device with magnetic properties may be to coat the medical device or a portion thereof with coating(s) or layer(s) 1922b, 1922c, which have magnetic properties, such as is shown in FIG. 19b-c. Such a coating may include magnetic materials such as are described above, or may be any known material which has been rendered magnetic through exposure to a electric and/or magnetic field(s) of sufficient strength. The coating(s) or layer(s) 1922b, 1922c may be ionized to facilitate deposition of the particles on the target surface of the medical device. As noted herein above, FIG. 19d shows a cutaway view of a section of the lattice portion 1915 with a center portion filled with magnetic material 1922d which may also be employed in accordance with embodiments of the present invention.

Figure 20:
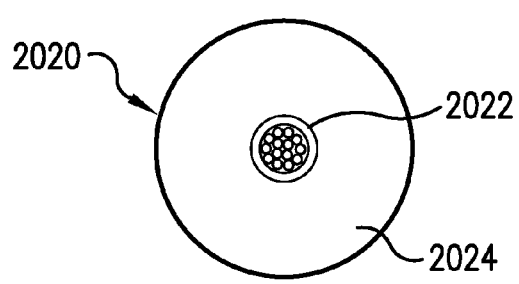
FIG. 20 shows a particle that may be employed in accord with the present invention.

As seen in FIG. 20, a coating particle 2020 comprising a core and shell is provided. The core includes magnetic material 2022 such as magnetic nanoparticles. The shell includes a therapeutic agent 2024. The therapeutic agent 2024 may be polymer-free. The particles 2020 can be provided in various forms. For example, in FIGS. 16-17, the particles 2120, 2220 are provided in powder form, however, the particles may exhibit various forms (e.g. fluid, gas, etc.). The particles may be any suitable size or shape. In some instances, annular particles may be used which comprise a core and a shell wherein the shell is approximately fifty and the core is approximately two. In other embodiments, not shown, the shell may be comprised of a magnetic material and the core comprised of a therapeutic agent. Other arrangements are also possible.

Figure 21:
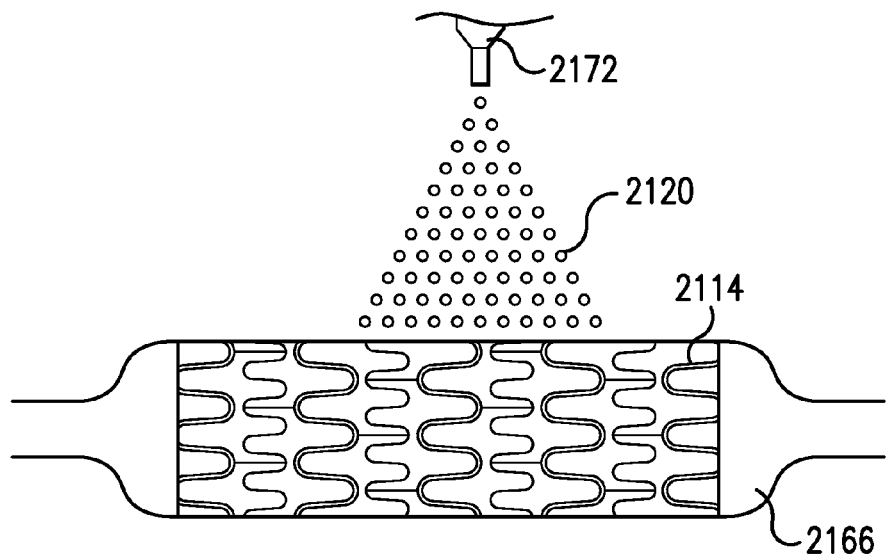
FIG. 21 shows a stent positioned on a holder and being coated with particles as may be employed in accord with the present invention.

As best seen in FIG. 21, the medical device 2114 may be positioned on a holder 2166 such as a balloon catheter. In certain instances, the holder 2166 may be resilient. In FIG. 21, since the holder 2166 is positioned on the inside of the lattice portion of the medical device 2114, the holder 2166 may also mask non-target surfaces of the medical device 2114, which, in the exemplary case, is the inner diameter of the medical device. Other arrangements are possible, for example, the outer diameter of the medical device 2114 may be masked.

Also as seen in FIG. 21, the particles 2120 may be directed at the medical device with a conventional fluid pressure source 2172. In FIG. 21, fluid pressure may be used to direct the particles 2120 at the target surface of the medical device 2114, however, any suitable delivery means may be used. Since, in the example the particles 2120 have a core containing magnetic material, the particles 2120 will be attracted to the magnetic portion of the medical device 2114 and adhere to a surface thereof.

Figure 22:
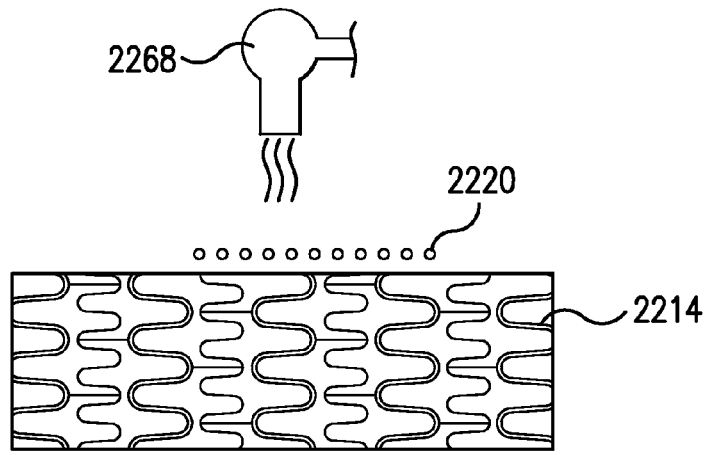
FIG. 22 shows heat being applied to a coated stent as may be employed in accord with the present invention.
Figure 23:
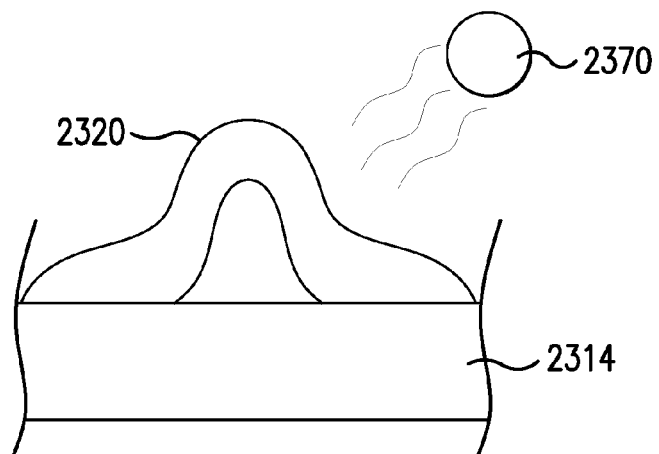
FIG. 23 shows a particle being fused to a stent target surface as may be employed in accord with the present invention.

As seen in FIGS. 22-23, prior to, during, or after the particles 2220 are directed at and adhere to the medical device, heat can be applied to the medical device 2214, 2314 using a conventional heating source 2268. As best seen in FIG. 23, the heated medical device 2314 fuses the particles 2320 adhered to the target surface of the medical device 2320 thereby releasing the therapeutic agent to deliver the therapeutic agent to the target surface of the medical device 2320.

Figure 24:
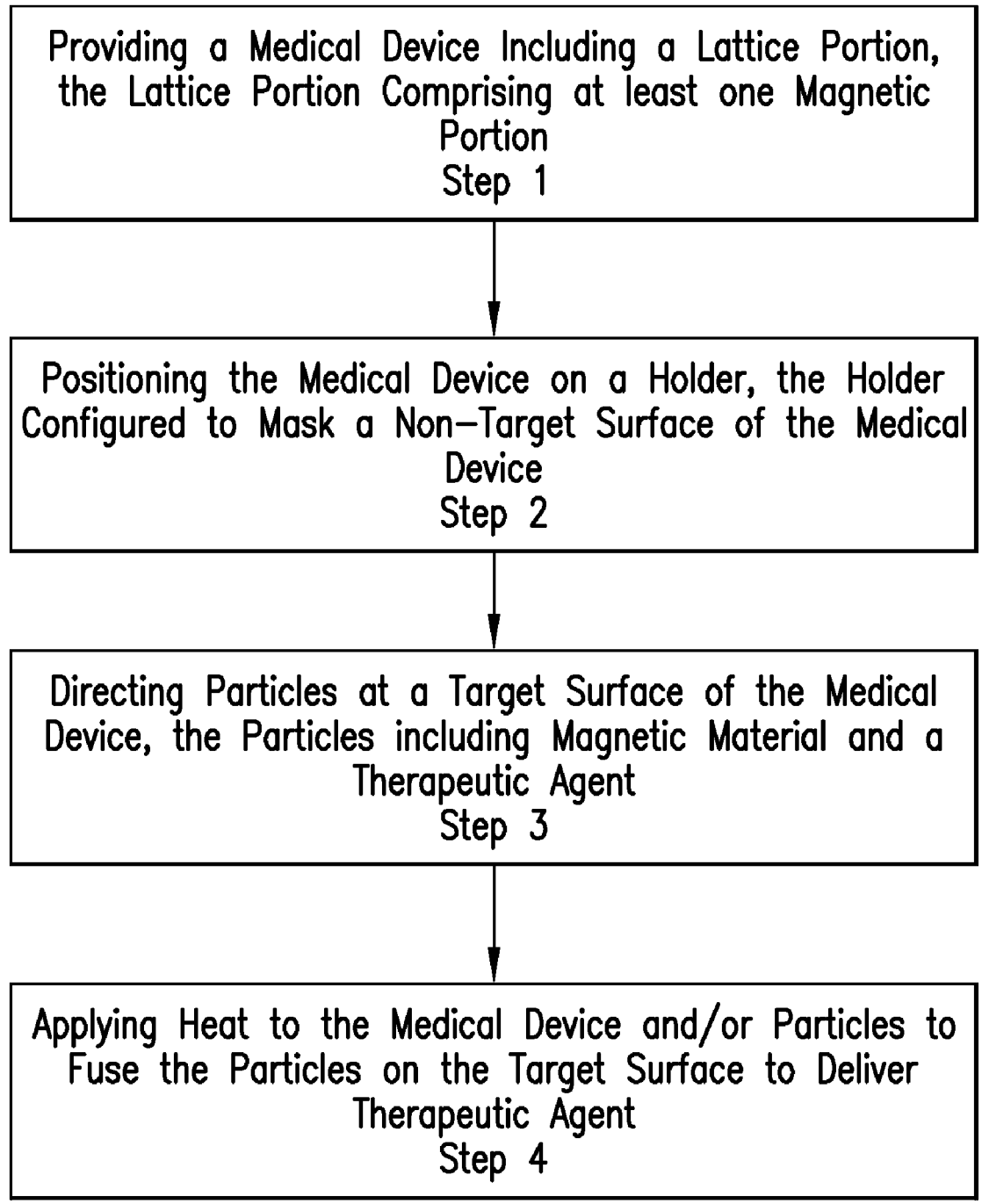
FIG. 24 shows method steps that may be employed in accord with the present invention.

FIG. 24 shows a flow chart including method steps that may be employed with embodiments of the present invention to coat a target portion of a medical device. In the example of FIG. 24, step 1 may include providing a medical device including a lattice portion which comprises at least one magnetic portion. Step 2 may include positioning the medical device on a holder, the holder configured to mask a non-target surface of the medical device. Step 3 may include directing particles at a target surface of the medical device, the particles including magnetic material are attracted to the medical device and adhere to a surface of the medical device. Step 4 may include applying heat to the medical device to fuse the particles adhered on the target surface to deliver therapeutic agent to the target surface. In alternative embodiments, not shown, the sequence of steps may be reordered and steps may be added or removed. The steps may also be modified. Further, the steps may be repeated in continuous fashion.

While various embodiments have been described, other embodiments are plausible. It should be understood that the foregoing descriptions of various examples of the medical device and delivery systems are not intended to be limiting, and any number of modifications, combinations, and alternatives of the examples may be employed to facilitate the effectiveness of delivering therapeutic agent to a medical device.

The coating, in accord with the embodiments of the present invention, may comprise a polymeric and or therapeutic agent formed, for example, by admixing a drug agent with a liquid polymer, in the absence of a solvent, to form a liquid polymer/drug agent mixture. A suitable list of drugs and/or polymer combinations is listed below. The term "therapeutic agent" as used herein includes one or more "therapeutic agents" or "drugs." The terms "therapeutic agents" or "drugs" can be used interchangeably herein and include pharmaceutically active compounds, nucleic acids with and without carrier vectors such as lipids, compacting agents (such as histones), viruses (such as adenovirus, adenoassociated virus, retrovirus, lentivirus and α-virus), polymers, hyaluronic acid, proteins, cells and the like, with or without targeting sequences.

Specific examples of therapeutic agents used in conjunction with the present invention include, for example, pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; anti-proliferative agents such as enoxaprin, angiopeptin, rapamycin, angiopeptin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitrofurantoin; anesthetic agents such as lidocaine, bupivacaine, and ropivacaine; nitric oxide (NO) donors such as linsidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warfarin sodium, Dicumarol, aspirin, prostaglandin inhibitors, platelet inhibitors and tick antiplatelet factors; vascular cell growth promoters such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the insertion site. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor ∀ and ∃, platelet-derived endothelial growth factor, platelet-derived growth factor, tumor necrosis factor ∀, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMPs"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNAs encoding them.

Coatings used with the exemplary embodiments of the present invention may comprise a polymeric material/drug agent matrix formed, for example, by admixing a drug agent with a liquid polymer, in the absence of a solvent, to form a liquid polymer/drug agent mixture. Curing of the mixture typically occurs in-situ. To facilitate curing, a cross-linking or curing agent may be added to the mixture prior to application thereof. Addition of the cross-linking or curing agent to the polymer/drug agent liquid mixture must not occur too far in advance of the application of the mixture in order to avoid over-curing of the mixture prior to application thereof. Curing may also occur in-situ by exposing the polymer/drug agent mixture, after application to the luminal surface, to radiation such as ultraviolet radiation or laser light, heat, or by contact with metabolic fluids such as water at the site where the mixture has been applied to the luminal surface. In coating systems employed in conjunction with the present invention, the polymeric material may be either bioabsorbable or biostable. Any of the polymers described herein that may be formulated as a liquid may be used to form the polymer/drug agent mixture.

The examples described herein are merely illustrative, as numerous other embodiments may be implemented without departing from the spirit and scope of the exemplary embodiments of the present invention. Moreover, while certain features of the invention may be shown on only certain embodiments or configurations, these features may be exchanged, added, and removed from and between the various embodiments or configurations while remaining within the scope of the invention. Likewise, methods described and disclosed may also be performed in various sequences, with some or all of the disclosed steps being performed in a different order than described while still remaining within the spirit and scope of the present invention.

What is claimed is:

1. A method of loading therapeutic agent into a porous region of a medical device, the method comprising:
   providing a medical device having at least a portion thereof comprising a porous region, the porous region having a plurality of pores;
   combining therapeutic agent with magnetic particles, the magnetic particles comprising material that can be influenced by a magnetic force; and
   interfacing the previously combined therapeutic agent and magnetic particles with the porous region of the medical device, ex vivo, while the magnetic particles are exposed to a magnetic force that urges the magnetic particles and therapeutic agent into pores of the porous region.

2. The method of claim 1 wherein particles of therapeutic agent and magnetic particles are formed when the therapeutic agent and the particles are combined, the particles sized to fit within the pores of the porous region.

3. The method of claim 1, wherein the therapeutic agent is polymer-free.

4. The method of claim 1, wherein a the magnetic field is separated into a static and a dynamic vector, whereby the dynamic component is not along the same direction as the static component.

5. The method of claim 1, wherein the magnetic force is generated by material comprising the medical device.

6. The method of claim 1, wherein the magnetic force is generated by an electro-magnet.

7. The method of claim 1, further comprising dissolving the therapeutic agent into a solvent prior to interfacing the therapeutic agent and magnetic particles with the porous region of the medical device.

8. The method of claim 1, wherein combining the therapeutic agent with the magnetic particles includes adhering the therapeutic agent to the magnetic particle through the use of at least one of an amino acid or a protein.

9. The method of claim 1, wherein a coating of the medical device comprises the porous region of the medical device.

10. The method of claim 1, wherein the medical device is an expandable stent.

11. The method of claim 1, further comprising masking a portion of the medical device prior to interfacing the therapeutic agent and magnetic particles with the medical device.

12. The method of claim 1, further comprising applying a vacuum force to urge therapeutic agent into the pores of the porous region.

13. The method of claim 2 further comprising coating the particles with a coating.

14. A method of loading therapeutic agent into a porous region of a medical device, the method comprising:
   providing a medical device having at least a portion thereof comprising a porous region, the porous region having a plurality of pores;
   dissolving therapeutic agent into a solution;
   loading magnetic particles, which include material that can be influenced by a magnetic force, into the solution;
   immersing at least a portion of the porous region of the medical device into the solution; and
   applying a magnetic force to attract the magnetic particles and the therapeutic agent into the pores of the porous region,
   wherein the magnetic particles and the therapeutic agent are attracted into the pores of the porous region, ex vivo.

15. The method of claim 14, further comprising providing a magnet to apply the magnetic force.

16. The method of claim 14, further comprising providing an electromagnet to apply the magnetic force.

17. The method of claim 14, wherein the therapeutic agent is polymer-free.

* * * * *